(12) United States Patent
Haas

(10) Patent No.: US 8,772,045 B1
(45) Date of Patent: Jul. 8, 2014

(54) METHOD FOR EXPLOSIVES DETECTION

(76) Inventor: Jeffrey S. Haas, San Ramon, CA (US)

(*) Notice: Subject to any disclaimer, the term of this patent is extended or adjusted under 35 U.S.C. 154(b) by 4 days.

(21) Appl. No.: 13/068,937

(22) Filed: May 23, 2011

Related U.S. Application Data

(63) Continuation-in-part of application No. 10/703,303, filed on Nov. 7, 2003, now Pat. No. 8,252,602.

(51) Int. Cl.
*G01N 33/00* (2006.01)
*G01N 33/22* (2006.01)

(52) U.S. Cl.
CPC .................................... *G01N 33/22* (2013.01)
USPC ............................ 436/169; 422/68.1; 436/174

(58) Field of Classification Search
CPC .............. G01N 1/02; G01N 2001/007; G01N 2001/022; G01N 2001/028; G01N 21/78; G01N 31/22; G01N 33/22
USPC .................................. 422/68.1; 436/169, 174
See application file for complete search history.

(56) References Cited

U.S. PATENT DOCUMENTS

| | | | | |
|---|---|---|---|---|
| 5,035,860 | A * | 7/1991 | Kleingeld et al. | 422/413 |
| 7,294,306 | B2 * | 11/2007 | Haas et al. | 422/411 |
| 7,807,104 | B2 * | 10/2010 | Haas et al. | 422/418 |
| 7,867,445 | B1 * | 1/2011 | Haas et al. | 422/68.1 |
| 8,071,385 | B2 * | 12/2011 | Haas et al. | 436/50 |
| 8,088,332 | B2 * | 1/2012 | Haas et al. | 422/68.1 |
| 8,252,602 | B2 * | 8/2012 | Haas | 436/169 |
| 2005/0064601 | A1 * | 3/2005 | Haas | 436/162 |
| 2007/0003435 | A1 * | 1/2007 | Haas et al. | 422/58 |

* cited by examiner

*Primary Examiner* — Sam P Siefke
(74) *Attorney, Agent, or Firm* — Dennis W. Beech

(57) ABSTRACT

The present method and system may be used for detecting the presence of explosive elements. A sample element may be used to swipe an object for a test sample. The sample element may be positioned in a sample holder of a testing device having a heater. The heater may be programmed to heat the sample element and sample in a controlled manner through two temperature increases from approximately 35 degrees to 165 degrees centigrade in approximately 20 seconds. Prior to each temperature increase a first and second reagent fluid is applied to the sample holder, and during the temperature rise the sample holder is observed for the presence of various explosive elements by detecting colors as compared to a color chart. The color observations may be based on time and temperature variations using a testing device.

12 Claims, 3 Drawing Sheets

US 8,772,045 B1

METHOD FOR EXPLOSIVES DETECTION

CROSS-REFERENCE TO RELATED APPLICATIONS

This is a continuation-in-part patent application of U.S. patent application Ser. No. 10/703,303, filed on Nov. 7, 2003 now U.S. Pat. No. 8,252,602.

U.S. patent application Ser. No. 10/703,303 is pending.

BACKGROUND OF THE INVENTION

This invention relates to systems and methods for precisely detecting the presence of explosives, non-military homemade explosives (HME) and explosives residue at trace or bulk levels. The new system and method may provide a compact test unit that incorporates a test method that may allow testing of sample articles at a selected location. The detection method may provide a sequence of detection over a combination of applied heat profiles, time profiles, and sequence of reagents. The detection unit may use chemicals and other elements that reduce the hazard to a user.

Chemical detection of the presence of explosives and explosive residue has been known for many years. The methods and chemicals used in the past have tended to be cumbersome to transport and put into use at a selected site or location and the testing may have been time consuming. Special testing devices and apparatus may have been developed for specific explosives, but they may have been unreliable, limited to only a few classes of different explosive types, dangerous to the user due to the chemicals used, not reproducible at low level detection, or otherwise limited in capability of identifying an explosives contaminated site or object.

A previously used chemical explosives identification technique that may have been reasonably reliable is thin layer chromatography or TLC. Testing apparatus and methods have been developed including kits for on-site testing. The colorimetric devices and methods including those using a TLC plate may have shortcomings for effective, efficient testing, e.g., difficulty of use, length of time, solvent waste disposal, use of toxic chemicals, large work area, need for calibration, limited type or number of explosive compounds detectable, use of glass as well as other issues.

The use of colorimetric testing or spot tests may have been recognized for many years as chemical reagents and methods were identified to detect the presence of a particular explosive. The colorimetric tests may afford quick results, may be easy to perform and may be sensitive relative to the explosive sample content, but may be limited in the number of different explosives detected. The most common spot test method may be to have explosives react with a base, then allow time or heat the sample, then perform a Griess reaction test, and then allow more time or heat the sample. Various formulations of the Griess reagent may have been developed. Also numerous types of substrates, sorbent materials or swipes, such as, wool, cotton, polyfabrics, porcelain spot plates, TLC plates, corvettes, beakers, jars and the like may have been used to perform testing. All of these testing devices and methods may have been limited in the past as discussed above making them cumbersome and unwieldy to use and thereby limiting the flexibility necessary for quick, site selected and timely testing for detection of the presence of explosives or explosive residue.

SUMMARY OF THE INVENTION

The present invention is directed to methods and systems for detecting the presence of explosive elements. A sample element may be used to swipe an object for a test sample. The sample element may then be positioned in a sample holder of a testing device after swiping and from which it is removable and the testing device having a heater. The heater may be programmed to heat the sample element and sample in a controlled manner through two temperature increases from approximately 35 degrees to 165 degrees centigrade in approximately 20 seconds. Prior to each temperature increase a first and second reagent fluid is applied to the sample holder, and during the temperature rise the sample holder is observed for the presence of various explosive elements by detecting colors as compared to a color chart. The color observations may be based on time and temperature variations using a testing device.

These and other features, aspects and advantages of the present invention will become better understood with reference to the following drawings, description and claims.

DETAILED DESCRIPTION

The following detailed description includes the best currently contemplated modes for carrying out the invention. The description is not to be taken in a limiting sense, but is made merely for the purpose of illustrating the general principles of the invention.

Figure 4:
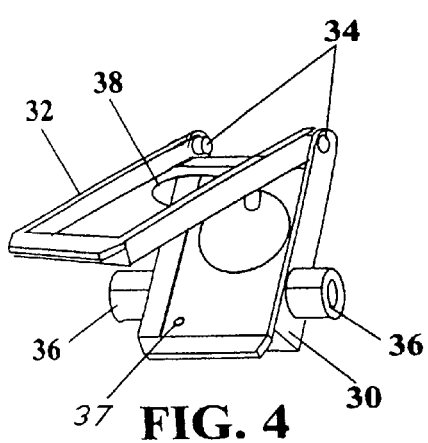
FIG. 4 illustrates a perspective view of the sample holder according to an embodiment of the invention.
Figure 1:
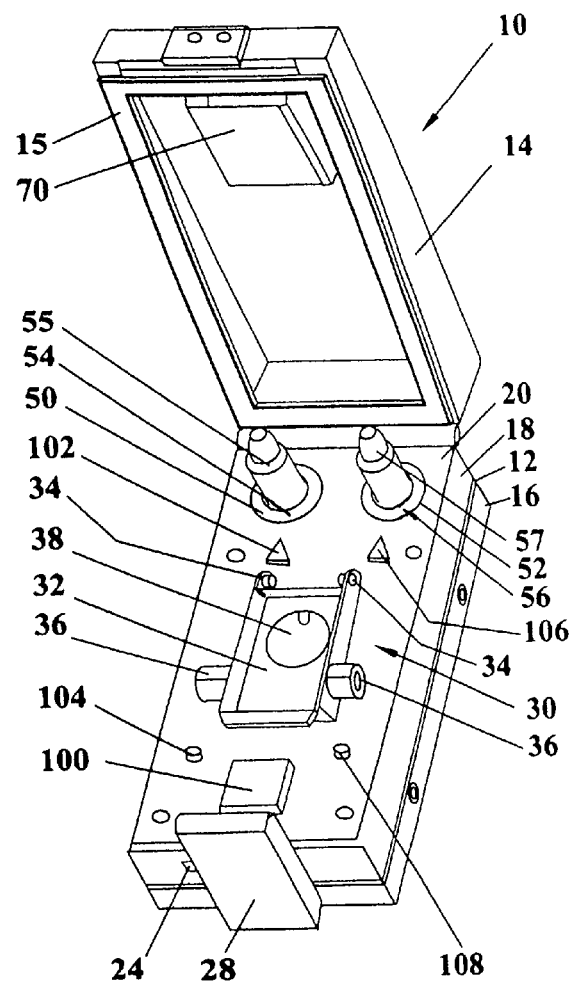
FIG. 1 illustrates a perspective view of a testing device according to an embodiment of the invention.
Figure 3:
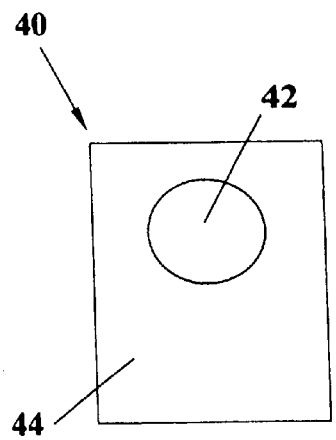
FIG. 3 illustrates a plan view of the sample element according to an embodiment of the invention.
Figure 3A:
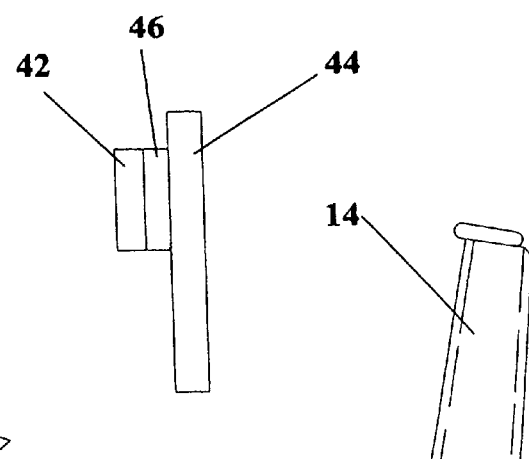
FIG. 3A illustrates a side view of the sample element according to an embodiment of the invention.
Figure 2:
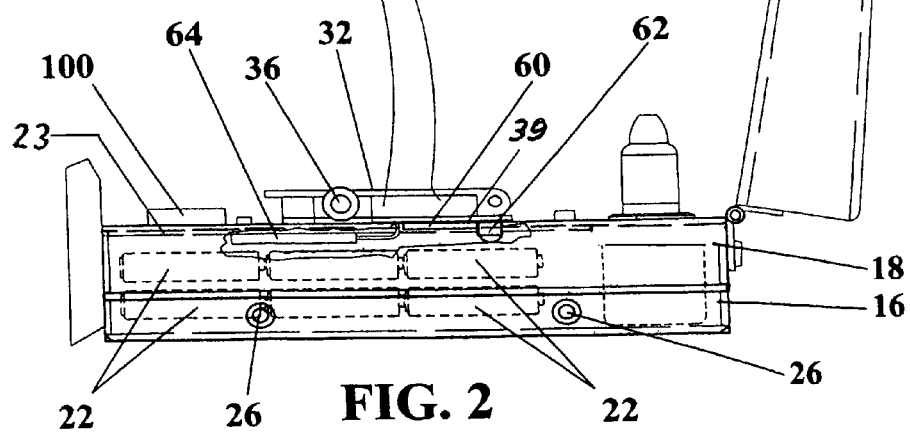
FIG. 2 illustrates a side elevation view of a testing device according to an embodiment of the invention.
Figure 5:
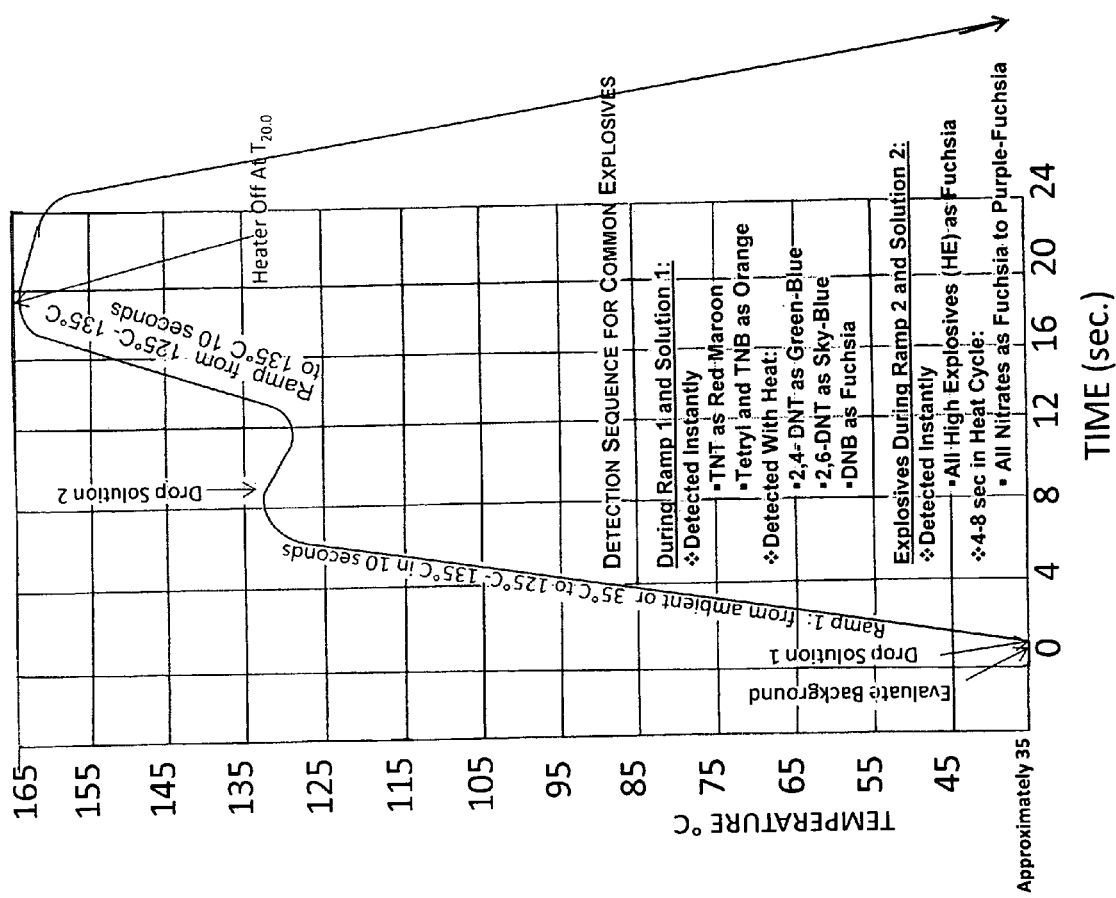
FIG. 5 illustrates a graph of the temperature versus time and reagent curve for an explosive test method according to an embodiment of the invention.

Referring to FIGS. 1 and 2, a colorimetric testing device 10 for various types of explosives and related energetic decomposition products, for example, nitro-, nitrate-, and nitramine-type explosives and other yet untested compositions may have a case 12 and cover 14 and may be easy to transport to a selected location for testing. Cover 14 may have storage bin 70 for retaining extra swipes or swabs. The test device 10 may allow reproducible and accurate testing of explosive samples as low as a few nanograms to saturated milligram levels on a substrate swipe. Cover 14 or case 12 may be fitted with an O-ring or gasket 15 to seal against moisture or dirt. There may be a case latch 28 for retaining the closed cover 14 to the case 12.

The case 12 may have a bottom 16 assembled with an enclosure 18 having an upper panel 20 that includes a programmable electronic controller board 23. There may be enclosure attachments 26 such as screws, bolts, quick release devices or the like for access to the batteries 22. The case 12 and cover 14 may be hinged or otherwise attached. Batteries 22 may be disposed in the case 12 with a power switch 24 positioned on the case 12 and a power on/off indicator 108. There may be a sample holder 30 attached to the upper panel 20 that may have a heater 60 disposed therein. The heater 60 may be in communication with the programmable electronic controller board 23 and batteries 22 and a temperature sensor 62. The sample retainer 32 may be in communication with the programmable electronic controller board 23 and batteries 22. There may also be a voltage regulator 64 to allow use of an external power source.

Referring to FIGS. 1 through 4, there may be a sample retainer 32 attached by a hinge 34 to hold a sample element 40 or swipe. The sample retainer 32 may have a retainer aperture 38 and may be held in place by spring ball retainers 36. The sample holder 30 may have a closed retainer sensor 37 that may be in communication with the programmable electronic controller board 23 and batteries 22. A flexible high temperature resistant foam pad 39 may insulate the heater 60 from the upper panel 20 and the sample holder 30. The high temperature resistant foam pad 39 may allow for uniform intimate contact of the sample element 40 against the heater 38 when the sample retainer 32 is closed. The sample element 40 may have a swipe pad 42 attached by pad attachment 46 to a backing element 44. The swipe pad 42 may be attached by adhesive, glue or other suitable element that maintains attachment and environment integrity up to approximately 165° C. without decomposing or other damage. The swipe pad 42 may be a defined size such as circular with an approximate diameter of 0.60 to 0.75 inches to accommodate test sample sizes and not require excessive use of reagent fluid. The pad attachment 46 may be chemically resistant and non-porous to inhibit the absorption of reagent fluid. The pad attachment, if for example adhesive, may also be of white color to not interfere with the visual evaluation of the swipe pad 42 during testing. If the pad attachment 46 is not positioned under the swipe pad 42, the backing element may be white colored in the area of the swipe pad 42. The pad attachment 46 may also be selected to minimize interference in heating swipe pad 42.

The swipe pad 42 may be formed of material that may be resistant to chemical degradation during testing in the approximate pH range of 1 through 14 at elevated temperatures over time to avoid reacting or decomposing. The swipe pad 42 may be white in color to aid test evaluation, may be heat resistant up to approximately 165° C. and may have hydrophilic properties for wetting using fluid reagents. The swipe pad 42 may also be roughened, for example, by use of a woven material, to aid in retrieving test sample particles from the environment. The swipe pad 42 may also be thick enough to resist damage such as tearing during sampling, yet not be too thick such that heating of the test sample is inhibited. When the sample element 40 may be positioned in the sample holder 30, the swipe pad 42 may be disposed relative to the retainer aperture 38.

Any geometric shape of swipe pad 42 may be used; however, a circular swipe pad 42 may provide for even wicking to the outer edges avoiding the occurrence of unwetted corners. It has been found by experiment that a swipe pad 42 circular shape with approximately 0.67 inch diameter and 0.001 inch to 0.003 inch thickness may allow an adequate test sample size of material to be wetted with a minimum use of reagent fluid. With a woven 100% continuous filament virgin polyester material, approximately 50 microliters of reagent may be sufficient for testing. Selecting swipe pad 42 characteristics may provide adequate surface area to perform the test sample collection or swiping task and reduce the volume of reagent necessary for transport with the testing device 10.

The backing element 44 may support the swipe pad 42 when in use for example to collect test samples. It may also protect the swipe pad 42 from contamination due to handling and may protect the swipe pad 42 from the heater 60. It has been found by experiment that a polyester material such as MYLAR may be used for the backing element 44. The polyester material may be resistant to chemical degradation and it may facilitate heat transfer to the swipe pad 42 without decomposing due to heating. The polyester material may be white in color to aid in test evaluation.

There may be a pair of cavities 50, 52 for positioning fluid containers 54, 56 in the case 12. The fluid container 54 may have cap 55 and the fluid container 56 may have cap 57. The fluid containers 54, 56 may have a reagent for use in testing a test sample for the presence of explosives or residues thereof. The fluid containers 54, 56 may be one of various types, for example, squeeze to release a drop of fluid, have a controlled dropper tip incorporated in the fluid container, have a pump or pump type cap to move fluid, or other fluid extraction method or structure.

Tetrabutylammonium hydroxide may be used in a reagent test to impart a color to nitroaromatic compounds that may otherwise not be detected by other bases, such as, sodium hydroxide or potassium hydroxide regardless of their respective concentrations. The tetrabutylammonium hydroxide may also be strong enough to create nitrite salts for other types of explosives that may be in the test sample in preparation for testing with a second type reagent. Use of tetrabutylammonium hydroxide may be difficult due to limited shelf life and its reaction to environmental carbon dioxide that may degrade the necessary color chemistry with nitroaromatics. To develop a solvent system mixable with water to inhibit degradation and reduce hazardous effects to a user, an ethanol and water mixture may be used to inhibit tetrabutylammonium hydroxide degradation with the ethanol ratio such as not to be flammable. The ethanol and water may also have minimum nitrite content to avoid reaction to a second type reagent test that may give false positive results. For example, if a 10 nanogram detection threshold may be used any nitrite content in the solutions may be less than 0.2 nanograms per microliter of fluid to minimize corruption of test results or false detection.

The first reagent test may use a first reagent fluid that may have an optimum detection performance range with the fluid having a tetrabutylammonium hydroxide in a water solution in the approximate range of 0.7 to 0.9 Molar and an ethanol as approximately 35 percent of the water solution. Test results may be obtained using a wider tolerance of elements in the first reagent fluid, but there may be reduced detection sensitivity. The tetrabutylammonium hydroxide in water solution may be in the approximate range of 0.1 to 1.53 Molar and the ethanol as approximately 5 to 95 percent of the water solution. Also, other alcohols or blends of alcohols may be used in place of ethanol; however, for example, methanol may be toxic to the user and isopropyl may be less toxic, but may have poorer detection sensitivity results and cause shorter shelf life for the reagent fluid.

A second reagent test may be a modified Griess reagent test. The Griess reagent may cause a highly colored azo dye to be created in a reaction with nitrite salts. The acid that may be used in the formulation of the second reagent may be phosphoric acid that may reduce hazardous effects to a user that may become a buffer during the reaction thereby buffering against itself to inhibit creation of too much acid on the swipe pad 42. Other types of acids that may be used in the Griess test may react too violently with the base, may be toxic or hazardous, or may create a strong odor.

The phosphoric acid may be mixed with sulfanilic acid and N-(1-naphthyl)ethylenediamine dihydrochloride. The sulfanilic acid may be water soluble with reduced toxicity and it may impart a light magenta to deep fuchsia-purple color to the test sample for ease of detection of explosives. N-(1-naphthyl)ethylenediamine dihydrochloride may be water soluble and not carcinogenic as with other salts, and may impart an effective color reaction from the test sample. The second reagent solution may use deionized water that may have minimum nitrite content to reduce false positive test results. For example, if a 10 nanogram detection threshold may be used any nitrite content in the solutions may be less than 0.2 nanograms per microliter of fluid to minimize corruption of test results or false detection.

The second reagent test may use a second reagent fluid that may have an optimum detection performance range with the fluid having a phosphoric acid in a water solution in the approximate range of 1.0 to 4.0 Molar; and a sulfanilic acid of approximately 8 grams with a N-(1-naphthyl)ethylenediamine dihydrochloride of approximately 5 grams per 1000 milliliters of the phosphoric acid in water solution. Test results may be obtained using a wider tolerance of elements in the second reagent fluid, but there may be reduced detection sensitivity. The phosphoric acid in water solution may be in the approximate range of 0.1 to 7.35 Molar, the sulfanilic acid may be in the approximate range of 5 to 8 grams, and the N-(1-naphthyl)ethylenediamine dihydrochloride may be in the approximate range of 5 to 9 grams. Other acids, acid combinations, or acid concentrations may be used, but may produce less than optimal testing sensitivity results. Other solutions may have increased acidity and be hazardous to the user as well as have a detrimental effect on the testing device. Other solutions may not be acidic enough for a detection reaction to occur or may be toxic. Other salts may be used, but they may reduce the explosives detection sensitivity.

There may be indicators and a mode switch 100 for use in facilitating the testing of a test sample and they may be in communication with said programmable electronic controller board 23 and batteries 22. An example configuration may be described in an example test method that may be used to test for explosives and related energetic decomposition products as follow.

Referring to FIGS. 1 through 5, a user may take a sample element 40 and swipe an object to be evaluated to obtain a test sample on the swipe pad 42. The sample element 40 may then be placed in the sample holder 30 and retained by the sample retainer 32. This action may activate a green LED arrow 102 to signal the user to add a first reagent in fluid container 54 to the swipe pad 42. When the first reagent fluid may be added the user may activate the mode switch 100 that may deactivate the green. LED 102 and activate the heater 60 as well as when repeating a second cycle with the green LED 106 at a later time. The green LED 102 and 106 may be in communication with said programmable electronic controller board 23 and batteries 22 to indicate which solution is to be dispensed at the proper time.

The heater 60 may heat to a temperature of approximately 135 degrees C. in approximately 8 to 10 seconds. During the temperature rise from approximately 35 degrees centigrade to 135 degrees centigrade in approximately 10 seconds, the presence of TNT as a red maroon color, and tetryl and TNB as an orange color may be detected on applying the first reagent fluid. The detection of 2,4 DNT as green-blue, 2,6 DNT as sky-blue, and DNB as fuchsia may occur 3 to 10 seconds after the TNT.

At the approximate temperature of 135 degrees centigrade the green LED arrow 106 may be activated to signal the user to apply the second reagent fluid from container 56 to the swipe pad 42. The mode switch 100 may be activated to cause the heater 60 to heat from approximately 135 degrees to 165 degrees centigrade within the next 10 to 15 seconds. With the application of the second reagent fluid the presence of all High Explosives (HE) as a fuchsia color may be detected immediately. The detection of nitrates as a purple-fuchsia color may occur in approximately 4 to 8 seconds after the HE. The heater 60 may be programmably deactivated at approximately 20 to 25 seconds of operation.

During the test method described above, if there is a described color change in the test sample after the first reagent in fluid container 54 may be applied, after the heating of the test sample or after the addition of the second reagent, there may be explosive material in the test sample.

While the invention has been particularly shown and described with respect to the illustrated embodiments thereof, it will be understood by those skilled in the art that the foregoing and other changes in form and details may be made therein without departing from the spirit and scope of the invention.

I claim:

1. A method for detecting the presence of explosive elements comprising:
   a) swiping an object to obtain a test sample using a sample element having a swipe pad;
   b) placing said sample element in a sample holder in a testing device and retaining said sample element with a sample retainer;
   c) applying a first reagent fluid that is a solution of a tetrabutylammonium hydroxide, an ethanol and a water from a fluid container on said swipe pad;
   d) activating a heater disposed under said sample element;
   e) heating said swipe pad to a first temperature from approximately 35 degrees to approximately 135 degrees centigrade to activate said first reagent fluid with said test sample;
   f) viewing said swipe pad to observe any color change in said test sample;
   g) applying a second reagent fluid that is a solution of a phosphoric acid, a sulfanilic acid, N-(1-naphthyl)ethylenediamine dihydrochloride and a water from a second fluid container on said swipe pad;
   h) activating said heater;
   i) heating said swipe pad to a second temperature from approximately 135 degrees to approximately 165 degrees centigrade to activate said second reagent fluid with said test sample; and
   j) viewing said swipe pad to observe any described sequence of color change in said test sample over time and heat profile that may occur.

2. The method as in claim 1 wherein said first temperature heating is completed in approximately 8 to 10 seconds and said second temperature heating is completed in approximately 8 to 10 seconds.

3. The method as in claim 1 wherein said swipe pad has an approximately circular shape of approximately 0.67 inch diameter and an approximate thickness of 0.001 to 0.003 inches.

4. The method as in claim 1 wherein said swipe pad is formed of a woven approximately 100 percent continuous filament virgin polyester material.

5. The method as in claim 1 wherein approximately 20 to 50 microliters of said first reagent fluid and later after heating, 20 to 50 microliters of said second reagent fluid are applied to said swipe pad.

6. The method as in claim 1 wherein said tetrabutylammonium hydroxide in said water solution is in the approximate range of 0.1 to 1.53 Molar, and said ethanol is between approximate 5 and 95 percent of said water solution.

7. The method as in claim 1 wherein said tetrabutylammonium hydroxide in said water solution is in the approximate range of 0.7 to 0.9 Molar, and said ethanol is approximately 35 percent of said water solution.

8. The method as in claim 1 wherein:
said phosphoric acid is in a water solution in the approximate range of 1.0 to 4.0 Molar; and
said sulfanilic acid is approximately 8 grams mixed with said N-(1-naphthyl)ethylenediamine dihydrochloride of approximately 5 grams per 1000 milliliters of said phosphoric acid in said water solution.

9. The method as in claim 1 wherein:
said phosphoric acid is in a water solution in the approximate range of 0.1 to 7.35 Molar; and
said sulfanilic acid is approximately 5 to 8 grams mixed with said N-(1-naphthyl)ethylenediamine dihydrochloride of approximately 5 to 9 grams per 1000 milliliters of said phosphoric acid in said water solution.

10. A method for detecting the presence of explosive elements comprising:
swiping an object to obtain a test sample using a sample element having a swipe pad that is an approximately circular shape of approximately 0.75 inch diameter and an approximate thickness of 0.002 to 0.005 inches;
placing said sample element in a sample holder in a testing device and retaining said sample element with a sample retainer;
applying a first reagent fluid of approximately 20 to 50 microliters from a fluid retainer on said swipe pad;
activating a heater disposed under said sample element;
heating said swipe pad to a temperature to activate said first reagent fluid with said test sample;
viewing said swipe pad to observe any described sequence of color change in said test sample over time and heat profile;
applying a second reagent fluid of approximately 20 to 50 microliters from a second fluid retainer on said swipe pad; and
viewing said swipe pad to observe any described sequence of color change in said test sample over time and heat profile.

11. The method as in claim 10 wherein said temperature is approximately 150° C.

12. The method as in claim 10 wherein said swipe pad is formed of a woven approximately 100 percent continuous filament virgin polyester material.

\* \* \* \* \*